(12) United States Patent
Bicker et al.

(10) Patent No.: US 11,772,128 B2
(45) Date of Patent: *Oct. 3, 2023

(54) PLASMA TREATMENT APPARATUS FOR PRODUCING COATINGS

(71) Applicant: Schott AG, Mainz (DE)

(72) Inventors: Matthias Bicker, Mainz (DE); Manfred Lohmeyer, Nackenheim (DE); Hartmut Bauch, Ober-Olm (DE)

(73) Assignee: SCHOTT AG, Mainz (DE)

( * ) Notice: Subject to any disclaimer, the term of this patent is extended or adjusted under 35 U.S.C. 154(b) by 371 days.

This patent is subject to a terminal disclaimer.

(21) Appl. No.: 16/854,523

(22) Filed: Apr. 21, 2020

(65) Prior Publication Data

US 2020/0316644 A1 Oct. 8, 2020

Related U.S. Application Data

(62) Division of application No. 13/980,729, filed as application No. PCT/EP2012/000162 on Jan. 17, 2012, now abandoned.

(30) Foreign Application Priority Data

Jan. 20, 2011 (DE) .................. 10 2011 009 057.6

(51) Int. Cl.
  *B05D 3/14* (2006.01)
  *C03C 17/28* (2006.01)
  (Continued)

(52) U.S. Cl.
  CPC ........... *B05D 3/147* (2013.01); *A61M 5/3129* (2013.01); *B05D 1/62* (2013.01); *B05D 7/22* (2013.01);
  (Continued)

(58) Field of Classification Search
  CPC ......... A61M 5/3129; A61M 2005/3131; H01J 37/32394
  See application file for complete search history.

(56) References Cited

U.S. PATENT DOCUMENTS 4,767,414 A 8/1988 Williams
4,822,632 A 4/1989 Williams
(Continued)

FOREIGN PATENT DOCUMENTS

DE 10224395 12/2003
DE 10314067 10/2004
(Continued)

OTHER PUBLICATIONS

Surface tension prediction of vegetable oils using arlilficial neural networks and multiple linear regression, Melo-Espinosa et al.. Energy Procedia 57 ( 2014 ) 886-895.
(Continued)

*Primary Examiner* — Michael C Miggins
(74) *Attorney, Agent, or Firm* — Ruggiero McAllister & McMahon LLC

(57) ABSTRACT

An apparatus and to a method for treating layers using a plasma zone sealed from the outer atmospheric pressure are provided. The apparatus and method include a plasma reactor including a substrate carrier in form of a container receiving means, and a closing element that is joined with the substrate carrier by means of a lifting device.

17 Claims, 9 Drawing Sheets

(51) Int. Cl.
  *H01J 37/32* (2006.01)
  *B05D 1/00* (2006.01)
  *B05D 7/22* (2006.01)
  *C03C 17/00* (2006.01)
  *A61M 5/31* (2006.01)

(52) U.S. Cl.
  CPC ............ *C03C 17/004* (2013.01); *C03C 17/28* (2013.01); *H01J 37/32394* (2013.01); *A61M 2005/3131* (2013.01); *B05D 2201/00* (2013.01); *B05D 2203/35* (2013.01); *B05D 2259/00* (2013.01)

(56) References Cited

U.S. PATENT DOCUMENTS

| | | | |
|---|---|---|---|
| 5,444,540 | A | 8/1995 | Dragotta |
| 5,456,940 | A | 10/1995 | Funderburk |
| 5,775,506 | A | 7/1998 | Grabenkort |
| 7,428,807 | B2 * | 9/2008 | Vander Bush ........ A61M 5/002 422/23 |
| 10,071,397 | B2 | 9/2018 | Bicker |
| 2004/0050960 | A1 | 3/2004 | Godfrey |
| 2004/0144733 | A1 | 7/2004 | Cooper |
| 2004/0231926 | A1 | 11/2004 | Sakhrani |
| 2007/0187280 | A1 | 8/2007 | Haines |
| 2008/0071228 | A1 | 3/2008 | Wu |
| 2009/0010985 | A1 | 1/2009 | Sakhrani |
| 2009/0304549 | A1 | 12/2009 | Coulson |
| 2010/0298738 | A1 | 11/2010 | Felts |
| 2011/0313363 | A1 * | 12/2011 | D'Souza ................ A61L 29/14 427/2.28 |

FOREIGN PATENT DOCUMENTS

| | | |
|---|---|---|
| DE | 102005040266 | 3/2007 |
| DE | 102009041132 | 4/2011 |
| EP | 0201915 | 1/1990 |
| EP | 1860140 | 11/2007 |
| EP | 2147988 | 1/2010 |
| GB | 2107923 | 5/1983 |
| WO | 9414183 | 6/1994 |
| WO | 2011029628 | 3/2011 |

OTHER PUBLICATIONS

Ionic Liquids as Grease Base Liquids, Mozes et al., Lubricants, Aug. 2017.

International Search Report dated Jul. 7, 2012 corresponding to International Application PCT/EP2012/000162. see 37 CFR 1.98d certification.

German Office Action (with English translation) dated Nov. 17, 2011 corresponding to German Patent Application 10 2011 009 057.6. see 37 CFR 1.98d certification.

International Preliminary Report on Patentability dated Jul. 25, 2013 corresponding to International Application PCT/EP2012/000162. see 37 CFR 1.98d certification.

Garrison, "Glow discharge plasma deposited hexafluoropropylene films: surface chemistry and interfacial materials properties", ELSEVIER, Thin Solid Fils, 352,(1999) 13-21.

MatWeb Material Property Data for Fomblin M100 accessed at http://www.matweb.com/search/DataSheet.aspx?MatGuid=0dd62fee08174f73ab7c1d5091ef30c5 on Oct. 13, 2022.

* cited by examiner

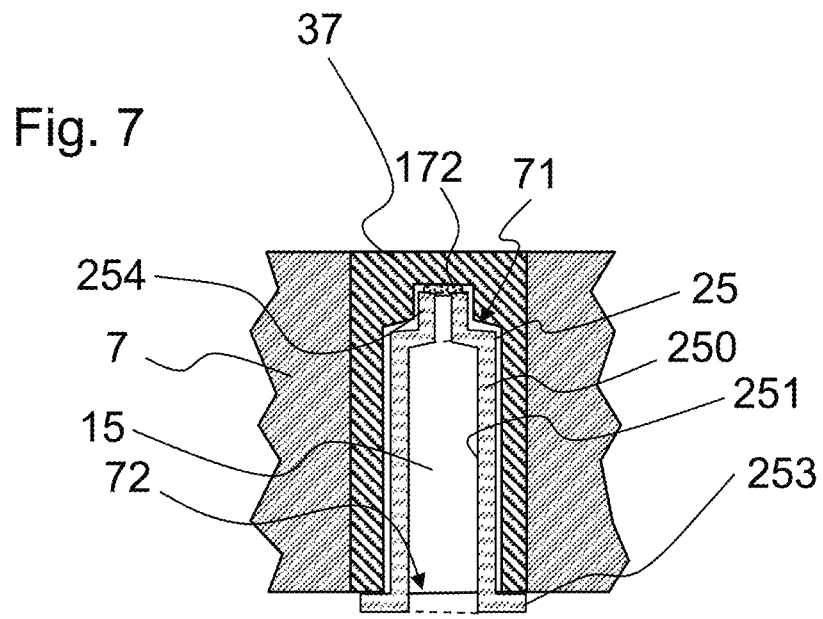
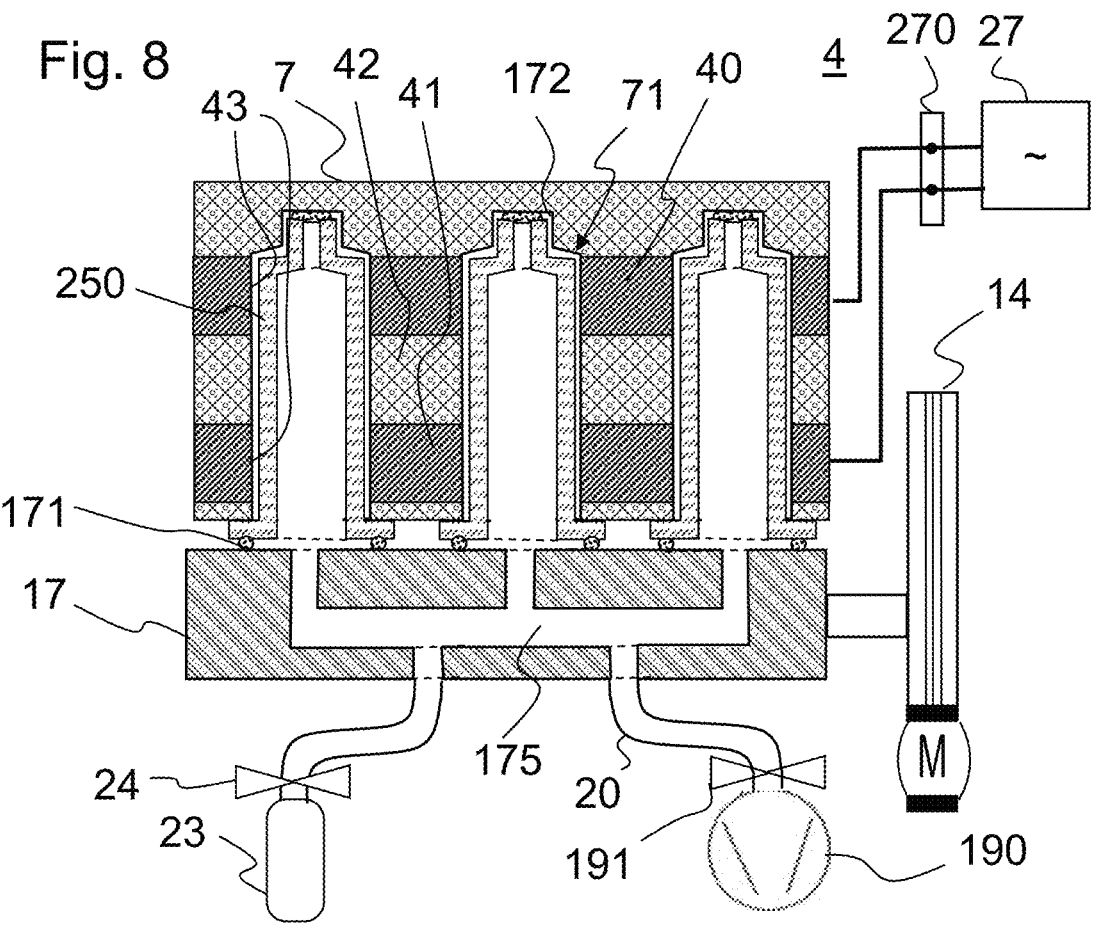

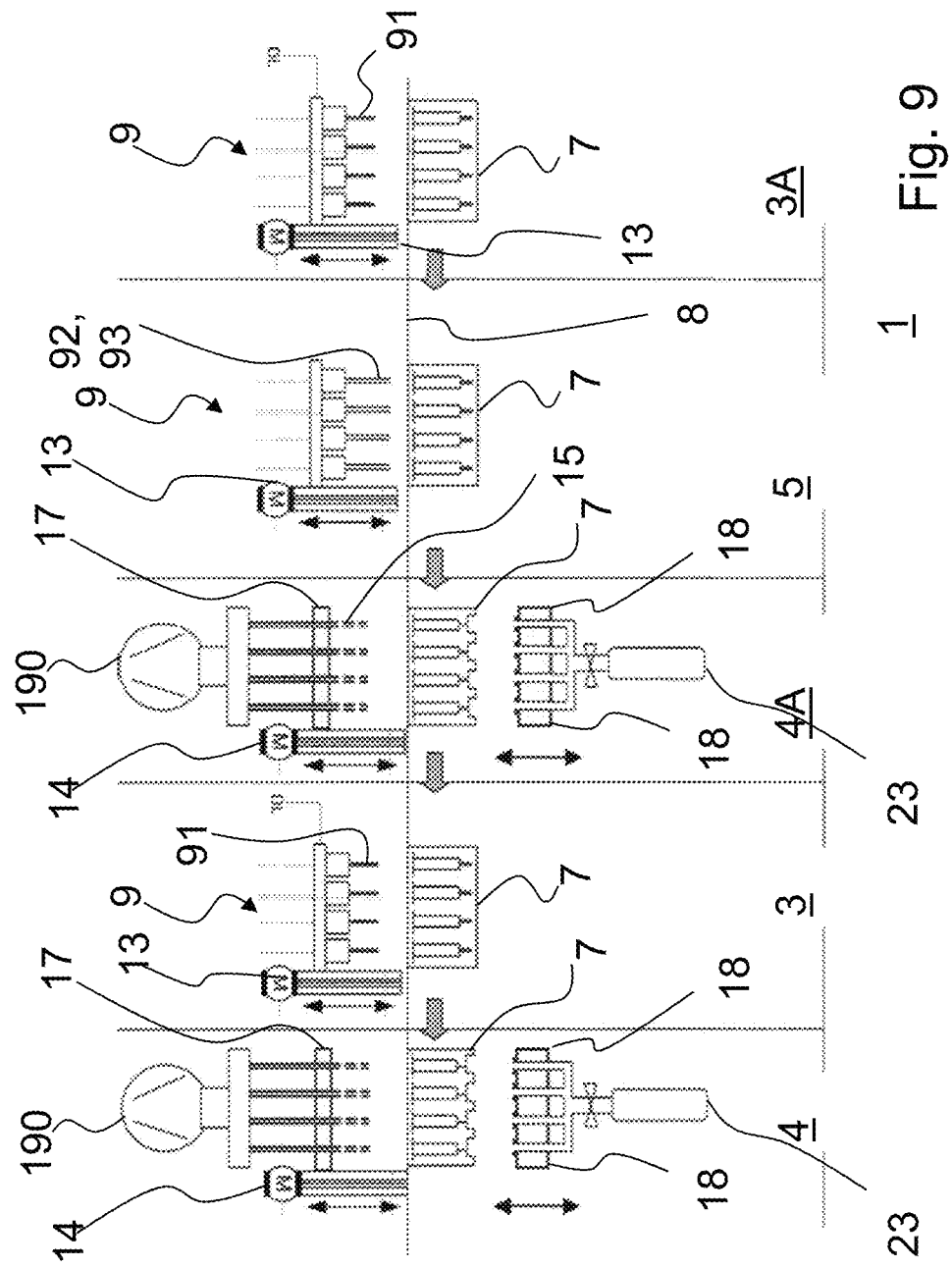

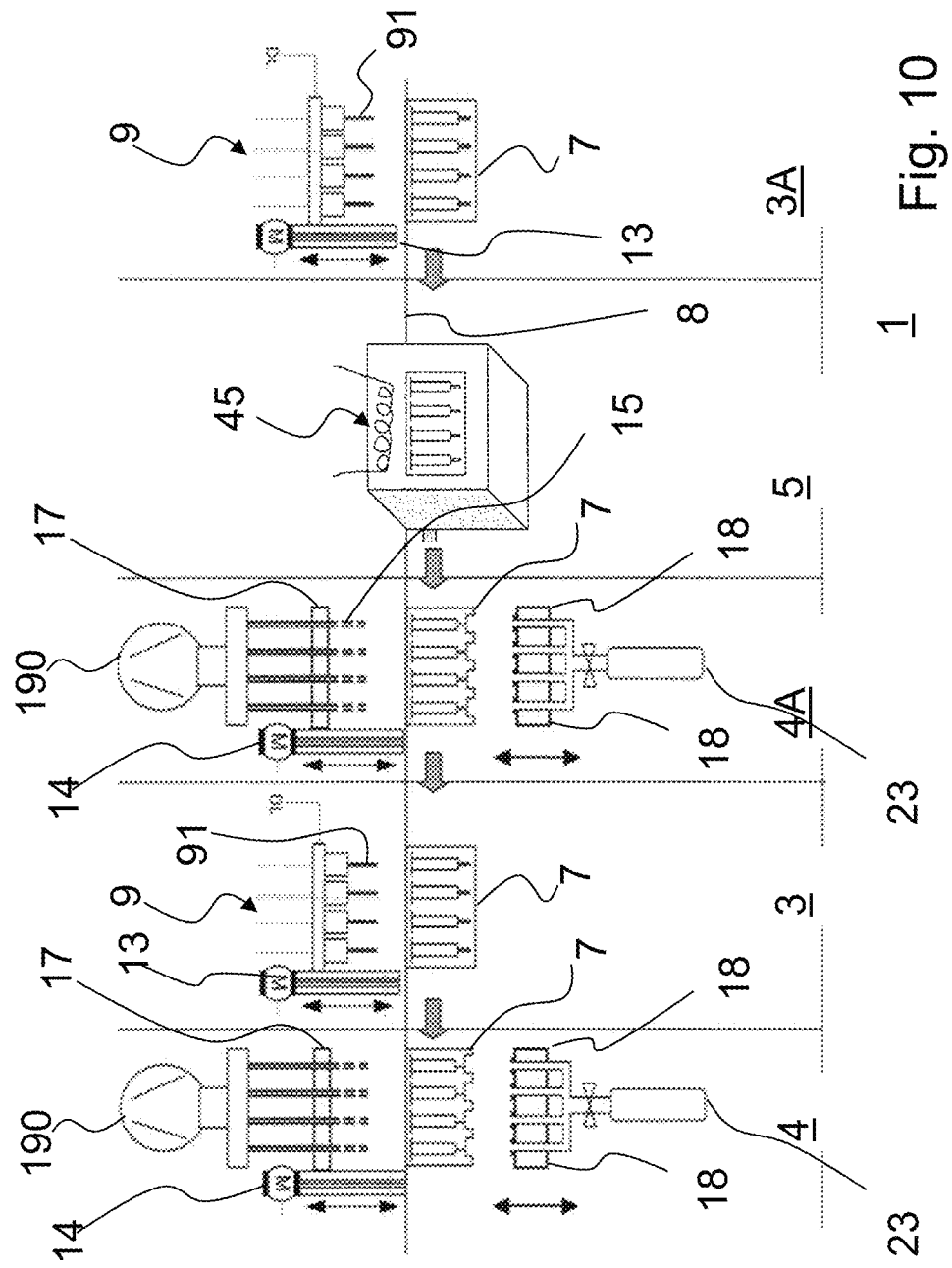

PLASMA TREATMENT APPARATUS FOR PRODUCING COATINGS

CROSS REFERENCE TO RELATED APPLICATIONS

This application is a divisional of U.S. application Ser. No. 13/980,729 filed Sep. 6, 2013, which is a national stage of International Application PCT/EP2012/000162 filed Jan. 17, 2012, which claims the benefit of German Application 10 2011 009 057.6 filed Jan. 10, 2011, the contents of all of which are incorporated herein by reference.

BACKGROUND

1. Field of the Invention

The invention generally relates to the technical field of treating surfaces and coatings using a plasma. More particularly, the invention relates to an apparatus and to a method for treating layers using a plasma zone that is sealed from the outer atmospheric pressure.

2. Description of Related Art

Plasma treatment methods for treating hollow body substrates are known from DE 10 2005 040 266 A1, DE 103 14 067 A1, and DE 102 24 395 A1. According to DE 103 14 067 A1 and DE 102 24 395 A1, a reaction chamber is formed by sealingly bringing together a sleeve-shaped wall member and a substrate carrier or chamber bottom. The substrate to be treated is disposed at the chamber bottom or substrate carrier. DE 10 2005 040 266 A1 describes an arrangement in which process gas flows through the treatment zone between opposite ends of a pharmaceutical packaging to be coated. The methods described in these documents are in particular intended to apply a plasma coating to the inner surface of the substrates.

From the prior art, silicone oil-based lubricating layers are known that have found application in various industrial sectors. Especially for parenteral pharmaceutical packaging such as syringes and carpules, silicone oils are commonly used as lubricating layer systems. For example, U.S. Pat. No. 4,767,414 A describes a method for reducing the static and dynamic friction between sliding surfaces by applying a lubricating film to at least one of the surfaces. To this end, a low molecular weight silicone oil is applied to one of the surfaces. The silicone oil and the surface are plasma treated.

However, some biopharmaceutical products are silicone oil intolerant, so that they do not exhibit sufficient stability in conventional siliconized packagings, such as siliconized prefilled syringes. One known reason for this silicone oil intolerance is that silicone oil tends to form particles thereby causing a silicone oil particle induced protein aggregation.

Therefore, new packaging solutions are currently sought by the market, to allow for shelf-stable storage of biopharmaceuticals in a silicone-free prefilled syringe system ("PFS=prefillable syringe"). What is needed therefor is a new lubricating layer system that meets the requirements on the tribological properties of friction partners syringe body/stopper while exhibiting low surface interaction with the biomolecules of the drug formulation.

US 2004/0231926 A1 discloses a method for producing a lubricating layer, wherein the lubricating layer is cured at atmospheric pressure using an atmospheric pressure plasma, inter alia. In addition to silicone oil-based coatings, perfluoropolyether-based lubricating layers can be prepared. The breakaway force or static friction of the latter layers, however, has turned out to be greater when compared to cured silicone oil layers. Moreover, in an atmospheric pressure treatment, in particular an atmospheric pressure plasma treatment, an introduction of gases, in particular of reaction products of the plasma into the layer may increase.

From DE 10 2009 041 132 A1 a method is known for producing a pharmaceutical packaging, wherein in a first process step a silicone-free fluid is applied to the inner surface of a pharmaceutical packaging, in particular a syringe body or a carpule, and in a second step the applied film is cross-linked using a low-pressure glow discharge.

SUMMARY

An object of the invention is to provide for an efficient production of lubricating coatings having improved properties, in particular in terms of sliding properties, storage stability, and compatibility with the contents of the packaging.

According to the invention, an apparatus for plasma treatment of containers is provided, comprising: at least one container receiving means including a container receiving chamber which has at least one open end through which a container to be treated is insertable in such a manner that an opening of the container faces the open end of the container receiving chamber. Furthermore, a closing element is provided, which can be brought together with the container receiving means by a lifting device, so that while closing by means of the lifting device by moving the closing element and the container receiving means towards each other a container accommodated therein is sealed from the outer atmospheric pressure at an opening thereof. For plasma treatment, a means is provided for generating at least one plasma zone sealed from the outer atmospheric pressure, comprising a pair of electrodes across which an electric or electromagnetic field is generatable in the interior of an accommodated and sealed container; wherein the means for generating a plasma zone further comprises means for removing atmospheric residual gas from the container via a gas-tight connection at the closing element. The apparatus further comprises at least one treatment tool which can be brought together with the open end of the container receiving chamber of the container receiving means for at least one sub-step of surface treatment of the containers, the treatment tool comprising means for applying an organic film to the inner surface of a container.

Preferably, the apparatus is configured as an integrated multi-chamber device for manufacturing silicone-free lubricating layers.

Accordingly, the apparatus comprises a plasma reactor with a substrate carrier in form of the container receiving means, and a closing element which is combined with the substrate carrier by means of a lifting device.

Furthermore, the plasma treatment apparatus comprises at least one treatment tool, for example in form of a spray nozzle or electrode, which is actively moved to the substrate carrier using a lifting device.

In a preferred embodiment of the invention, the apparatus comprises at least one station for spray-depositing a preferably non-silicone organic fluid using treatment tools appropriately adapted for spray-depositing the fluid, and a plasma treatment station concatenated thereto.

Specifically, an apparatus according to the invention for plasma treatment of workpieces, in particular containers, more particularly for inside plasma treatment of the containers, comprises at least one container receiving means including a container receiving chamber having an open end through which a container to be treated is insertable in such a manner that an opening of the container faces the open end of the container receiving chamber.

At least one closing element is provided, which closing element can be brought together with the container receiving means using a lifting device, so that when being closed using the lifting device by moving the closing element and the container receiving means towards each other, a received container is sealed at an opening thereof.

In a first embodiment of the invention, plasma treatment may be effected in an atmospheric pressure plasma. In this case, removing of the atmospheric residual gas means exchanging the atmospheric residual gas by a process gas.

However, more preferably, the plasma treatment is carried out in a low-pressure plasma. The larger mean free paths of the plasma particles allow for higher particle energies and therefore result in a particularly effective plasma treatment which may in particular comprise a crosslinking of the organic film.

According to a preferred embodiment of the invention, the apparatus is configured for generating a low-pressure plasma zone, by comprising a pair of electrodes across which an electric or electromagnetic field can be generated inside an accommodated and evacuated container; wherein the means for generating a low-pressure plasma further comprise a means for evacuating the container via a vacuum connection at the closing element.

In a further embodiment of the invention, the apparatus is adapted for treating containers having proximal and distal open ends, or first and second opposite ends, in the interior of the containers using a plasma. Especially syringe and carpule bodies are considered here. Preferably, for this purpose, the apparatus comprises at least two displaceable closing elements for closing the two openings. For example, by bringing together a first closing element at the proximal or first end and a second closing element at the distal or second end with the container receiving chamber and into a gas-tight connection with the containers, a plasma reactor is formed which is sealed from the outer atmospheric pressure.

The lifting device may be implemented, for example, using a linear axis or a pneumatic lifting cylinder.

Furthermore, for the plasma treatment, means are provided for generating a plasma zone sealed from the outer atmospheric pressure, in a preferred embodiment a low-pressure plasma zone, comprising a pair of electrodes across which an electric or electromagnetic field can be generated inside an accommodated and evacuated container.

A plasma zone sealed from the outer atmospheric pressure in the sense of the invention refers to a plasma within a spatially separated region, which is produced in a process gas, wherein the partial pressure(s) of the process gas differ from the outer atmospheric pressure by at least 1 mbar, preferably at least 5 mbar, more preferably at least 100 mbar.

A low-pressure plasma in the context of the invention refers to a plasma which is produced in a process gas with a process pressure in the container for plasma treatment preferably in a range from 0.01 mbar to 50 mbar, more preferably in a range from 0.5 mbar to 20 mbar, most preferably in a range from 1 mbar to 10 mbar.

Moreover, at least one treatment tool is provided which can be brought together with the open end of the container receiving chamber of the container receiving means for at least one sub-step of the surface treatment. Bringing together in this context preferably means that either the treatment tool is connected with the container receiving means or is inserted into the container receiving means to perform the surface treatment.

The treatment tool may in particular comprise a means for applying an organic film to the inner surface of a container to be processed by the plasma. Preferably, the organic film is spray-deposited as a liquid organic film using a spray nozzle.

By sealing a container accommodated in the container receiving means at the container opening which is brought together with the closing element using the lifting device, a separation of the plasma zone from the outer atmospheric pressure is achieved. In this manner, by closing the container with the closing element a plasma treatment chamber is formed, the wall of which is constituted by the inner wall of the container to be treated.

Accordingly, the method for inside plasma treatment of containers performable using the apparatus according to the invention is based on the process steps of: inserting a container which has an opening into an open end of a container receiving chamber of a container receiving means in such a manner that the opening of the container faces the open end of the container receiving chamber; bringing together a treatment tool with the open end of the container receiving chamber; applying an organic film by means of the treatment tool to the inner surface of the container inserted in the container receiving chamber; closing the container at the opening thereof by means of a closing element which is brought together with the container receiving means by actuating a lifting device, and sealing the container from the outer atmospheric pressure by means of the closing element; extracting atmospheric residual gas from the interior of the container via a gas-tight connection at the closing element using a suitable device; generating a plasma zone inside the container and treating the organic film by the plasma.

Particularly preferable, as mentioned above, a low-pressure plasma treatment is performed. According to this embodiment of the invention, therefore, the following process steps are performed: applying, by means of the treatment tool, an organic film to the inner surface of the container accommodated in the container receiving chamber; closing the container at the opening thereof by means of a closing element which is brought together with the container receiving means by actuating a lifting device, and sealing the container using the closing element; evacuating the interior of the container using a means for evacuating the container via a vacuum connection at the closing element; generating a low-pressure plasma in the interior of the evacuated container, and treating the organic film by the low-pressure plasma.

It has been found that a plasma treatment in an atmospheric pressure plasma for manufacturing organic cross-linked lubricating films has the following drawbacks:

Due to the low energy input from atmospheric pressure plasmas, only weak cross-linking can be achieved in the lubricating layer, and surface functionalization is ineffective because of the low excitation energies, since it will only be weakly pronounced due to the low excitation energy of the particles of the atmospheric pressure plasma. Furthermore, the particles excited by the atmospheric pressure plasma only have a low energy, so that they can only penetrate into and act in the outermost surface layers of the lubricating layers. Another drawback of the atmospheric pressure plasma process is the increased process costs due to the high gas flows required. The gas flows needed are higher by a factor of 10 to 1000 than in low-pressure glow discharge processes, and an expensive inert gas such as helium has to be used, which increases the operating costs. Moreover, with atmospheric pressure plasmas, undesirable toxic gases such as nitrogen oxides or ozone may be produced due to the contact of the plasma zone to the ambient air. An atmospheric pressure plasma usually has an inhomogeneous plasma zone. In most atmospheric pressure plasmas there are local areas of very high plasma intensity, such as for example in a corona discharge under atmospheric pressure as well as in an atmospheric dielectrically hindered discharge, in which filaments are formed in many cases. Therefore, local inhomogeneities are likely to be produced in the layer by the surface treatment.

In contrast, the low-pressure plasma treatment of the invention has the following advantages.

A more homogeneous surface treatment can be achieved as compared to atmospheric pressure plasmas, due to a homogeneous discharge zone within the container, especially streamers and filaments can be easily avoided in the discharge. This results in a more efficient and better cross-linking of the lubricating layer due to the higher energy input of the particles in the low-pressure glow discharge process as compared to the atmospheric pressure plasma. The penetration depth of the plasma particles into the lubricating layer is larger, thereby also cross-linking deeper layers of the lubricating layer. Decomposition products and volatile compounds are removed by the evacuation. Furthermore, a simultaneous pre-sterilization is possible and is more efficient than in atmospheric pressure plasmas, due to the higher energy input.

In a particularly preferred embodiment, a lance is provided as a component of the means for generating a low-pressure plasma, which lance may be introduced into the container interior of a container accommodated in the container receiving chamber, in particular by combining it with the closing element. The lance may have at least one of the following features: the lance is configured as one of the two electrodes, the electrode being designed as an internal electrode; the lance is configured as a gas manifold for introducing and distributing process gas for the low-pressure plasma; the lance is configured as a gas sucking means for extracting process gas.

Combining the lance and the displaceable closing element enables in a surprisingly simple manner to insert and position the treatment tool in form of the lance in the container and, at the same time, to achieve a sealing of the plasma chamber as well as electrical insulation of the plasma zone.

Furthermore surprisingly, simultaneously to the sealing of the plasma chamber by a displaceable closing element, a connection to the media supply may be accomplished:

In this preferred embodiment, the at least one displaceable closing element has at least one open passage with a port to a media supply via a gas-tight conduit. Media supply may be implemented in form of process gas or vacuum, so that the gas-tight conduit is connected to a compressed air reservoir containing process gas, or to a vacuum pump. Preferably, the apparatus further comprises a gas-tight, switchable valve in the gas conduit for connecting or disconnecting the media supply to/from the process chamber.

In a particularly preferred embodiment, the open passage of the one displaceable closing element is connected to a vacuum pump.

In another embodiment, furthermore, a second displaceable closing element is provided, which is connected to a compressed air reservoir for process gas.

Especially preferably, a cross-linkable film is applied as the organic film, which can then be cross-linked in the low-pressure plasma. Accordingly, it is suggested that the means for applying an organic film comprises a reservoir containing an organic compound that is cross-linkable in a plasma.

Process gases for the plasma treatment preferably include argon, helium, xenon, oxygen, nitrogen, or mixtures of these gases, more preferably argon, oxygen, nitrogen, or a mixture of these gases.

Materials that may be used as materials or components of the organic film, and optionally of further layers, in particular for enhancing the sliding effect, or additionally also to improve the adhesion of the organic film to the container, include the following: Perfluoropolyether (PFPE) such as the products marketed under the trade names of Fomblin M03, M30, M100, Y, Z, Fluorolink compounds; Perfluorosiloxanes; Lubricating layers containing polytetrafluoroethylene (PTFE) particles; Oils, such as mineral oil, vegetable oil, animal-based oil; Synthetic fluid hydrocarbons; Fluid fluorinated or chlorinated hydrocarbons; Organic esters such as fatty acid esters; Polyphenylethers; Phosphoric acid esters; Polyethylene or polyalkylene glycols; Polyalphaolefins; Polyaromatic hydrocarbons such as alkylbenzenes; Polyuretanes; Squalene.

Silicone-free organic films that are particularly preferably cross-linked in the plasma sealed from the outer atmospheric pressure, include fluoroalkyl and/or ethylene groups, preferably in form of a fluid including fluorinated or perfluorinated polyethers.

Preferably, perfluoropolyether compounds are used for the cross-linkable organic film, more preferably with the following molecular structure:

R1-(0-CF—R—CF2)p-(0-CF2)q-R2;

with p/q in a range from 0.1 to 1.0; and
with R=—CF3 or R=—F; wherein
functional groups R1, R2 are selected from the group of:
—CF3, —F, —OH, —CxHy—OH, —CH2—OH, CH2(OCH2CH2)rOH,
—CH2OCH2CH(OH)CH2OH, —CH2OCH2-piperonyl.

Therefore generally, according to this embodiment of the invention, a perfluoropolyether-containing organic film is applied and is cross-linked in the low-pressure plasma.

Furthermore, it is advantageous to wash and dry the containers just before applying the organic film, in particular when coating glass containers such as glass syringe bodies or glass carpules. Preferably, herein, the time offset between the cleaning step and the subsequent deposition of the organic film is less than 10 minutes, preferably less than 5 minutes, more preferably less than 30 seconds.

According to a preferred embodiment of the invention, the treatment steps are spatially separated. To this end, at least two treatment stations are provided. In this case it is particularly useful to use the container receiving means as a transfer container. For this purpose, a transfer means is provided for transferring the container receiving means between the treatment stations. A first one of the treatment stations comprises the means for applying the organic film to the inner surface of a container. A second one of the treatment stations is arranged downstream of the first treatment station in the transfer direction of the transfer means and comprises the means for generating a plasma zone sealed from the outer atmospheric pressure, preferably for generating a low-pressure plasma. Thus, the organic film previously applied in the first treatment station is treated by the low-pressure plasma in the second treatment station, wherein this treatment may in particular comprise a cross-linking of the film, as described above.

For simple motion sequences in the apparatus according to the invention, it is particularly advantageous if the treatment tool is also displaceable using a lifting device, like the closing element, to bring together the treatment tool and the container receiving means. In particular a treatment tool such as a spray nozzle may be introduced into the container in this manner.

In order to produce a uniform coating on the inner surface of the container, it has further proved to be advantageous for the containers to be held with their opening, or one of their openings in case of more than one opening, facing downwards, at least during the step of applying the organic film. Particularly preferable, the containers are supported with their longitudinal axis oriented vertically, but they may likewise be held obliquely. However, the longitudinal axis of the containers should preferably be oriented between the 9:00 and 15:00 directions, i.e. by not more than 45° from the vertical. When depositing the organic layer, this will result in a better uniformity of the film on the container. In case the containers are syringe bodies, this will prevent the spray-deposited film from accumulating in the shoulder region of the syringe body and from running into and blocking the Luer channel/needle mouth.

If the container has two opposite openings and different inside diameters at the openings, as is the case with syringe bodies and carpule bodies, inter alia, it is particularly advantageous if the containers are held with their opening having the larger inner diameter facing downwards. Accordingly, in one embodiment of the invention the apparatus is adapted for treating preferably cylindrically symmetric containers having a longitudinal axis, a distal end E1, and a proximal end E2, with different inner diameters, wherein the inner diameter $DE_1$ of the distal end is smaller than the inner diameter $D_{E2}$ of the proximal end, and wherein the apparatus is adapted to arrange the containers to have an orientation during the spraying with the ends E1 having the smaller inner diameter facing upwards, with the longitudinal axes thereof in a range from 0° to 45°, preferably in a range from −5° to 5°, to the vertical.

During the plasma treatment the container is also preferably supported with one of its openings facing downwards, in case of containers having a plurality of openings of different opening cross-sections preferably with the opening having the larger inner diameter facing downwards, with an orientation of the longitudinal axes thereof of no more than 45° out of the vertical. This prevents particles from falling into the hollow body. Moreover, when maintaining the orientation between the steps of coating and plasma treatment, container handling and the associated structural design of the apparatus will be simplified.

The invention is especially useful to provide pharmaceutical packaging with inside coatings. In particular, the invention can be used to produce silicone-free cross-linked organic lubricating layers which improve the sliding action of a plunger, for example in a pharmaceutical container in form of a syringe or carpule, and which exhibit good compatibility with the drug filled into the syringe. In the case of a syringe or carpule, sealing by the closing element is accomplished at the plunger opening. In particular in case of syringes an orientation of the syringes with their flange openings facing downwards has proved to be very advantageous for preventing particles from entering.

The invention will now be illustrated in more detail with reference to the accompanying figures. The same reference numerals in the figures designate the same or corresponding elements.

BRIEF DESCRIPTION OF THE DRAWINGS

FIG. 7 is a partial view of a container receiving means;
FIG. 8 shows another embodiment of a container receiving means comprising a pair of electrically separated outer electrodes with openings for receiving a plurality of syringe bodies, and with a displaceable closing element;
FIGS. 9-10 illustrate further embodiments of an apparatus for plasma treatment of syringe bodies.

DETAILED DESCRIPTION

The apparatus described below with reference to the figures, and the corresponding plasma treatment processes for containers performable with these apparatus specifically relate to the manufacturing of silicone-free lubricating layers for pharmaceutical syringes and carpules. The barrel of the syringe or carpule may be made of glass as well as from plastics. Durable coatings with a silicone-free lubricating anti-friction layer are possible on both of these materials. The following description in part specifically relates to the treatment of syringe bodies. However, the invention is equally applicable to carpules which, like syringes, also have a container in form of a barrel for receiving a plunger.

Plastics that are suitable for being surface coated or treated include in particular cyclo-olefin copolymers (COC) and cyclo-olefin polymers (COP), but alternatively also polyethylene in the form of HDPE, MDPE, and LDPE, as well as polypropylenes. Preferred glasses include borosilicate glasses.

Figure 1:
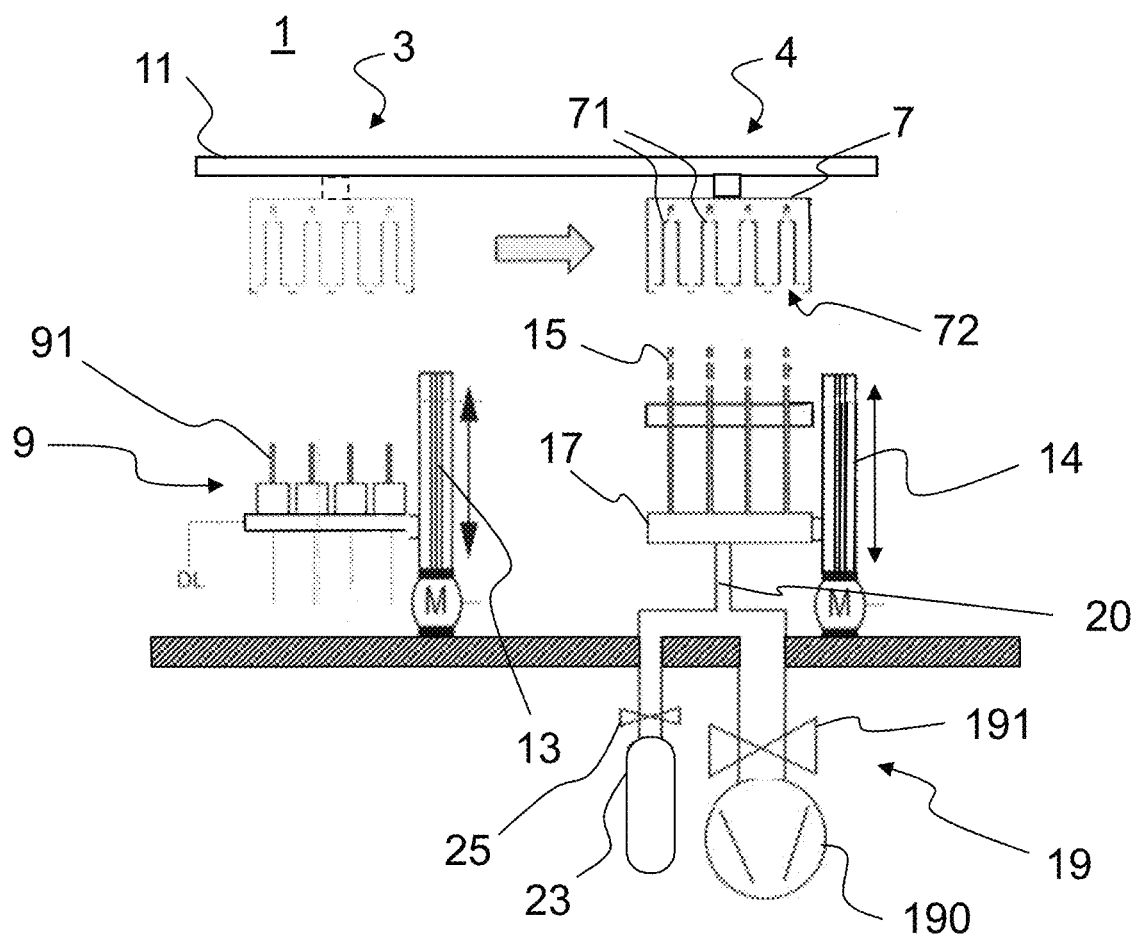
FIG. 1 is a schematic view of a first embodiment of an apparatus for plasma treatment of syringe bodies.

The apparatus 1 as shown in FIG. 1 comprises two treatment stations 3, 4 for the process steps of spray-depositing and curing of the organic films in the plasma. At treatment station 3, the organic film is applied to the inner surface of the containers, here specifically to the inner wall of the barrel of syringe bodies.

Then, in treatment station 4, cross-linking of the deposited films is accomplished in a low-pressure plasma. Preferably, a low-pressure glow discharge is employed for the plasma treatment, without being limited to the illustrated exemplary embodiment.

The apparatus according to the invention provides for coating with organic films, in particular organic lubricating layers, in a rapid succession in an integrated process, by enabling pre-coating (preferably by spray-depositing) with an organic fluid in a first treatment station 3, and subsequent cross-linking by a plasma treatment process in the second treatment station 4, with a total duration of the process steps of fluid coating in treatment station 3 and plasma-supported cross-linking in treatment station 4 of less than 30 seconds, preferably less than 10 s, more preferably less than 5 s.

Apparatus 1 comprises a container receiving means 7 having a plurality of container receiving chambers 71 which have an open end 72 through which the syringe bodies to be treated are inserted in a manner so that each of the plunger openings thereof faces the open end 72 of the container receiving chamber. According to one embodiment of the invention, without limitation to the illustrated example, it is particularly advantageous if the container receiving means comprises at least two, preferably at least four treatment chambers for simultaneous treatment of the containers. Accordingly, at least two, preferably four containers may thus be treated simultaneously in such a container receiving means using separated plasma treatment zones.

Container receiving means 7 is moved by a transfer means 11 in horizontal direction from treatment station 3 to treatment station 4 which is arranged adjacent to treatment station 3. Generally, without limitation to the example shown in FIG. 1, the apparatus 1 including the transfer means may be configured as a clocked linear batch system or as a clocked rotary system or circular rotary table.

Treatment station 3 serves to apply the organic film to the inner surface of the syringe or carpule barrel, and treatment station 4 arranged downstream of treatment station 3 in the transfer direction of the transfer means 11 comprises means for generating a low-pressure plasma in the syringe bodies in order to solidify the applied organic film, in particular for cross-linking and adhering it to the substrate surface.

Treatment tool 9 of treatment station 3 comprises a plurality of spray nozzles 91 which are introduced, by means of a lifting device 13, into the syringe bodies which are received in container receiving means 7 and positioned above the spray nozzles by the transfer means 11.

For distributing the liquid film of the organic fluid on the inner surface of the syringe or carpule barrel, in one embodiment of the invention the spray nozzles 91 may generally be moved during the spray-depositing in an axial direction along the syringe or carpule barrels, using lifting device 13. Preferably, the spray nozzles are moved at a speed ranging from 1 mm/s to 200 mm/s.

Generally it is advantageous, without limitation to the specific configuration of the exemplary embodiment shown in FIG. 1, when spray-depositing the organic film while axially moving a spray head or a spray nozzle 91 with a stroke speed in a range from 1 mm/s to 1000 mm/s, preferably in a range from 5 mm/s to 200 mm/s, more preferably in a range from 8 mm/s to 50 mm/s. Spray-depositing is preferably performed at a rate of more than 0.1 µl/s, most preferably more than 0.3 µl/s.

Preferred amounts of fluid for the application of the organic film are in a range from 0.004 µl/cm$^2$ to 2.8 µl/cm$^2$, more preferably in a range from 0.009 µl/cm$^2$ to 0.22 µl/cm$^2$. This permits to obtain complete fluid films which on the other hand are thin enough to achieve a continuous cross-linking in the low-pressure plasma treatment.

Furthermore, it is favorable for the lubricant layer to be produced from a fluid having a viscosity in a range from 1 to 10,000 centi-Stokes, with a viscosity index (according to the ASTM D 2270 standard) of greater than 80, preferably greater than 100, more preferably greater than 150. On the one hand, this allows to produce small droplets of liquid during spray-depositing, and on the other a running of the film is suppressed and thus inequalities in layer thickness are prevented.

Once the treatment step of spray-depositing, by means of treatment tool 9, of an organic film to the inner surface of the syringes or carpules placed in the container receiving chambers 71 has been completed, treatment tool 9 is retracted from container receiving means 7 by lifting device 13, so that the container receiving means 7 may now be conveyed to treatment station 4 by transfer means 11.

Treatment station 4 comprises one lance 15 for each of the container receiving chambers 71. The lances 15 are arranged at a closing element 17.

Generally, without being limited to the illustrated exemplary embodiment, the treatment tool such as lance 15 or the internal electrode is fixed to the closing element. If, as in the illustrated exemplary embodiment, an internal electrode is used to generate the field for the low-pressure plasma, it is generally advantageous to introduce the internal electrode into the container at least up to half the length of the container. This is advantageous in order to achieve a sufficiently strong field in substantially the entire volume of the container.

Closing element 17, in turn, is arranged on a lifting device 14 and is displaceable together with the lifting device 14, like the spray nozzles 9 of treatment station 3, in an axial direction along the syringe or carpule barrels.

Treatment station 4 comprises means for generating a low-pressure plasma, comprising a pair of electrodes across which an electric or electromagnetic field can be generated in the interior of a received and evacuated syringe barrel. For plasma treatment of the applied organic film, first the closing element 17 is brought together with the container receiving means 7 by means of lifting device 14, and in this sealing operation using lifting device 14 by moving closing member 17 and container receiving means 7 towards each other the syringes or carpules are sealed at their openings by the closing element. Moreover, when bringing together container receiving means 7 and closing element 17, lances 15 are introduced into the syringe barrel.

Connected to closing element 17 is a means 19 for evacuating the syringe barrels via a vacuum connection 20 at closing element 17. Means 19 for evacuating comprises a vacuum pump 190 and a valve 191. Vacuum connection 20 may be implemented by flexible connections, preferably gas-tight hoses, like the process gas supply.

The gas-tight conduit system, i.e. including the vacuum connection in the example shown in FIG. 1, may generally be implemented using flexible hoses. The process gas supply may likewise be realized with a flexible hose. The flexible hoses will allow the closing element 17 to be displaced.

Valve 191 may constitute or comprise a throttle valve. Without being limited to the exemplary embodiment shown in FIG. 1, one embodiment of the invention provides for a pressure control in the plasma zone in the interior of the containers to be treated by means of such a throttle valve arranged at the connection to the vacuum pump, and using a pressure control means acting on the throttle valve.

Without being limited to the specific configuration of the exemplary embodiment, the embodiment of FIG. 1 is based, inter alia, on a movement along two axes of movement, a horizontal movement of the container receiving means, and a vertical movement by which the treatment tools are introduced and the syringe bodies are brought together with and sealed by the closing element at the end of the plunger openings.

A process gas reservoir 23 including a metering valve 24 serves to fill the evacuated syringe barrels with a suitable process gas, under low-pressure. The process gas is introduced into the syringe barrels through lances 15. Evacuation may also be achieved through the lances, via separate openings therein, or through an opening in the closing element.

Figure 2:
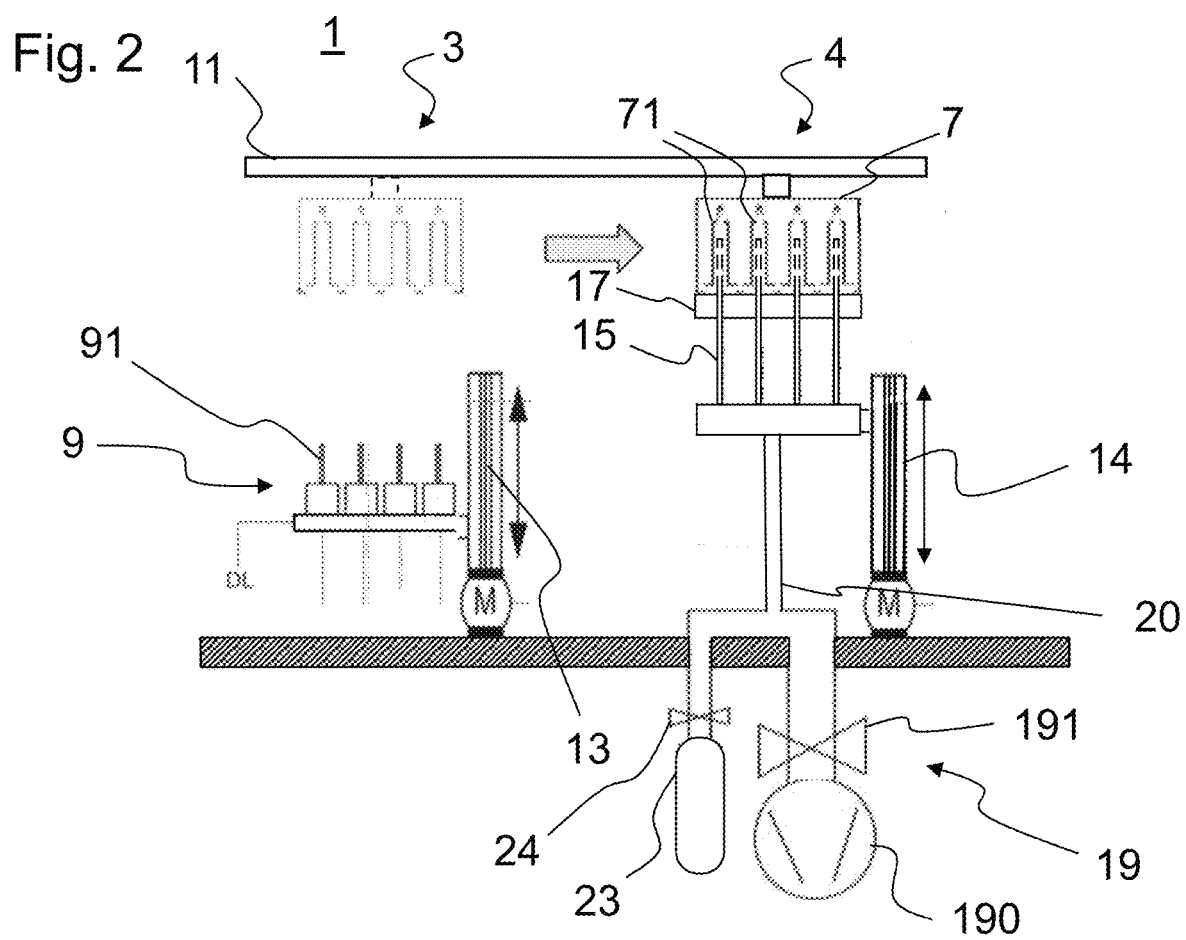
FIG. 2 shows the apparatus with the reactor closed.

FIG. 2 shows apparatus 1 with the reactor closed. Here, closing element 17 has been brought together with container receiving means 7 by means of lifting device 14. Now the syringe bodies may be evacuated internally, filled with process gas, and a low-pressure plasma may be ignited in the syringe bodies. Lance 15 serves as an internal electrode, the container receiving means 7 forms the outer electrode.

Filling with gas, especially the process gas used, and pumping out may be performed simultaneously. An advantage thereof is that the residual gas is removed quickly by the purging procedure. Preferably, a duration of purging (pumping out while introducing gas) is less than 60 seconds, preferably not more than 10 seconds, more preferably not more than 5 s.

In the configuration shown in FIGS. 1 and 2, the internal electrode is in direct contact with the plasma. For such electrodes in contact with the plasma zone, preferably a corrosion-resistant metal is commonly used, preferably aluminum or an aluminum containing alloy.

At least one of the electrodes is connected to a high frequency AC voltage source. If only one of the electrodes is connected, the other electrode is coupled to a reference potential, for example ground potential. The applied high-frequency AC voltage produces an electromagnetic field between the electrodes and consequently also inside the syringe bodies evacuated and filled with process gas at a low-pressure. The field then causes the generation of a plasma in the interior of the syringe body. Preferably, voltages and pressures are chosen such that a low-pressure glow discharge is generated.

Figure 3:
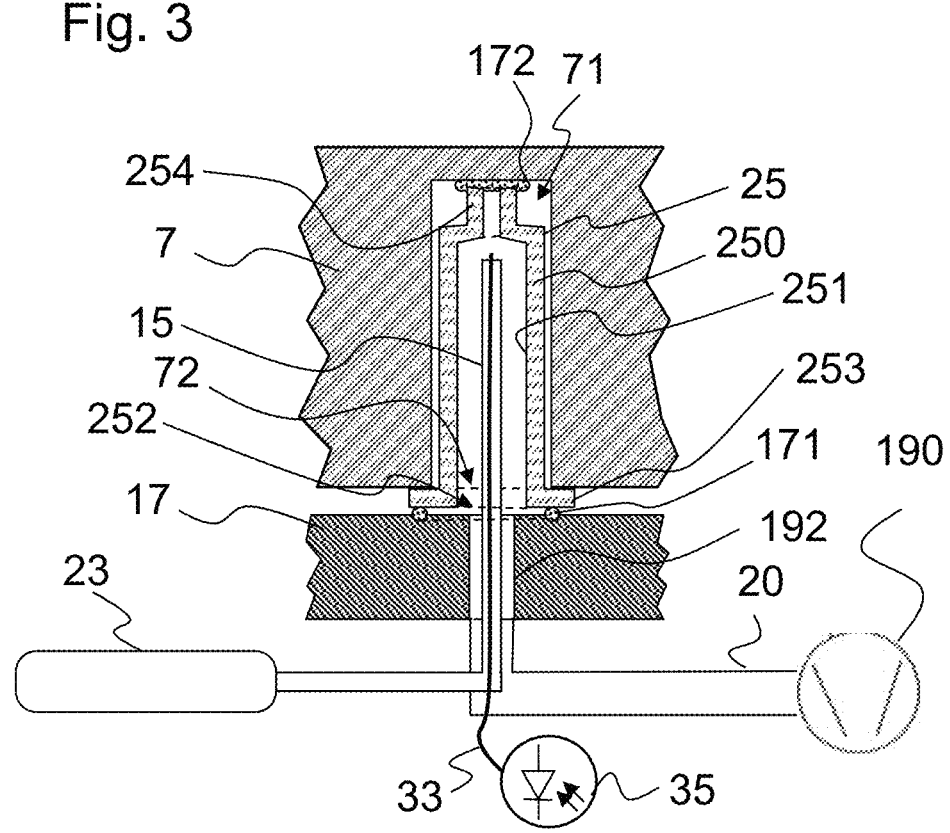
FIG. 3 shows details of the apparatus including container receiving means and closing element.

FIG. 3 illustrates, in a schematic cross-sectional view, details of apparatus 1. Specifically, FIG. 3 is a partial view of container receiving means 7 that has been brought together with closing element 17 at the treatment station 4 for plasma treatment.

A syringe body 25 is inserted and fixed in container receiving chamber 71 in such a manner that the opening thereof, in particular the plunger opening 252, faces the open end 72 of container receiving chamber 71. The plunger opening at the end of syringe barrel 250 is surrounded by a flange 253 or finger rest.

Closing element 17 includes a sealing element 171, in this case specifically in form of a sealing ring. When, as shown in FIG. 3, the container receiving means 7 is brought together with the closing element 17 by the lifting device, the syringe body will be sealed at its plunger opening 252 by sealing element 171. Another sealing element 172 is provided in container receiving chamber 71 and seals the nozzle 254 of the syringe body which is often referred to as a syringe Luer taper. According to an advantageous embodiment of the invention, the sealing element 172 sealing the Luer taper may be designed in a manner to simultaneously clamp the syringe or carpule body, so that the syringe or carpule body is retained in container receiving chamber 71. Suitable for this purpose is a sealing element 172 in form of a sealing ring or sealing lip which upon insertion of the syringe or carpule body laterally engages the Luer taper or, more generally, the end of the syringe or carpule body opposite the plunger opening under elastic deformation.

Accordingly, in a preferred embodiment of the invention, without being limited to the illustrated exemplary embodiment, generally at least two sealing elements or sealing points are provided per container receiving chamber.

Sealing elements 171, 172 allow to achieve a vacuum tight sealing of the syringe body 25, in particular a vacuum tight seal with respect to atmospheric pressure with a leak rate of less than $5 \times 10^1$ mbar·l/s. Thus, the syringe body 25 is sealed at both ends and may be evacuated through suction opening 192 by vacuum pump 190.

In the embodiment shown in FIG. 3, lance 15 for introducing and distributing the process gas extends through suction opening 192. Of course, other configurations are likewise possible, for example with one or more suction openings 192 arranged adjacent lance 15, or, as mentioned above, with a lance that has both inlet openings for the process gas and suction openings.

The evacuated zone, i.e. the interior of the syringe body 25, then also defines the zone in which the plasma can be generated. This plasma zone is confined by the inner surface 251 of the syringe body. For the sake of simplicity, the organic film on inner surface 251 which is applied during operation of the apparatus and solidified by the plasma, in particular cross-linked, is not shown in FIG. 3.

As shown in FIG. 3 by way of example, a light guide 33 may be provided, which directs light from container receiving chamber 71 to a photodetector 35. With this arrangement, the plasma may be monitored. In a modification of the invention, it is also possible to control the plasma treatment process by taking into account the measured values of the photodetector. The fiber end of light guide 33 is preferably located directly inside the reactor chamber. Preferably, the fiber is extended through the electrode assembly, for example through lance 15 as shown in FIG. 3, so that the fiber is directly introduced into the syringe body 25 and directly extracts the plasma light. By contrast, if photodetection is accomplished through the container, due to the glass or plastic material certain frequency ranges might not be transmitted or might at least be partially absorbed, depending on the material, whereby light detection becomes difficult. The arrangement with the fiber end inside the container provides measured data which are not influenced by the container material. In order to enable a broadband detection of the plasma light, preferably a light guide is used which transmits infrared radiation, visible light, and UV light.

Figure 4:
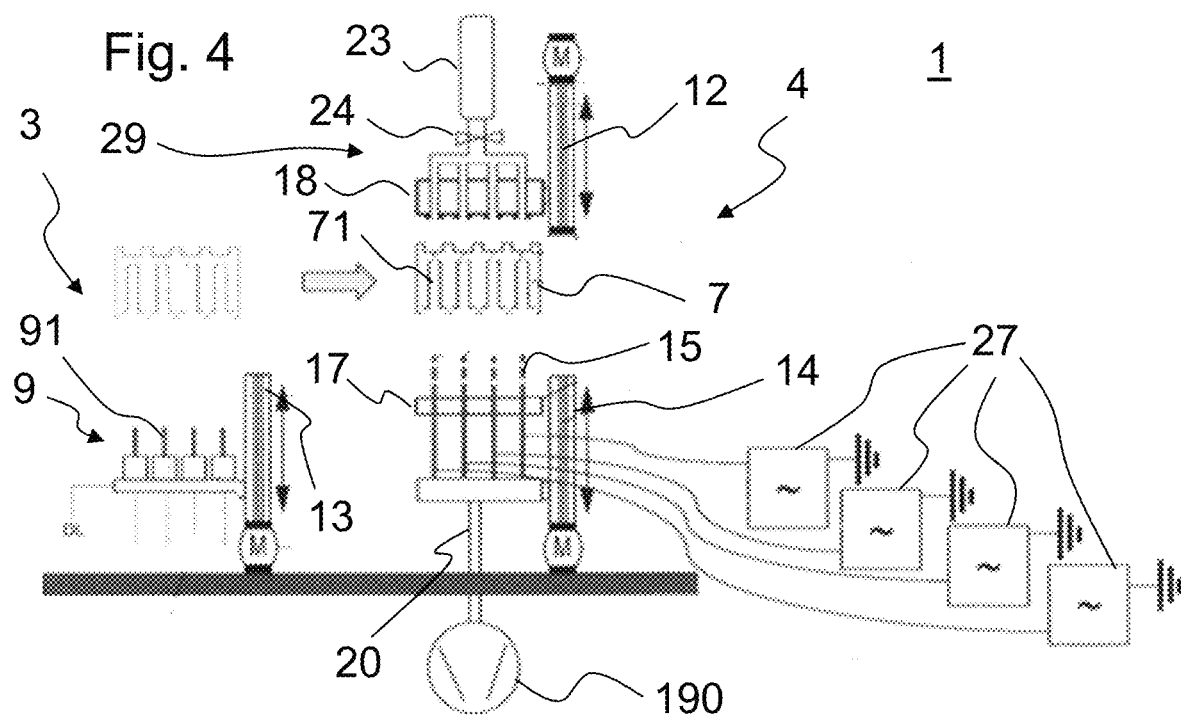
FIG. 4 shows another embodiment of the invention.

According to yet another embodiment of the invention, lance 15 is used for evacuation, and the process gas is introduced through nozzle 254 of the syringe body. An exemplary embodiment is shown in FIG. 4. Generally, without being limited to the specific embodiment illustrated, treatment station 4 comprises a further closing element 18 which is brought together with the container receiving means opposite to closing element 17, and which seals the plasma chambers of plasma treatment station 4 formed by the syringe bodies. In a modification of this embodiment of the invention, evacuation may be effected at this further closing member, or process gas may be introduced there, as illustrated. Thus, in the embodiment shown in FIG. 4, the further closing element 18 is part of a gas manifold 29.

According to still another embodiment of the invention, as shown, the further closing element 18 is brought together with the container receiving means 7 by a further lifting device 12. Alternatively, it is also possible to provide only one lifting device on one of closing elements 17, 18, in which case once this closing element has been brought together with the container receiving means 7, the stroke movement will entrain the container receiving means 7 to bring it together with the further closing element. For gas supply, in the case of at least partially stationary components of the gas manifold 29, one or more flexible hoses may be used for supplying gas to closing element 18, as already mentioned above.

Generally, without being limited to the specific configurations of the exemplary embodiments shown in the figures, the assembly of container receiving means 7 and transfer means is preferably substantially immobile in the vertical direction. This means that the assembly is preferably completely immobile in the vertical direction, or that the motion thereof, for example in case of the entraining of the container receiving means 7 mentioned above, is less than 10% of the lifting movement.

In the example shown in FIG. 4, a plurality of alternating voltage generators 27 are provided to supply the energy required for plasma generation. Here, a separate AC voltage generator 27 is provided for each of the container receiving chambers 71. As illustrated in FIG. 4, AC voltage generators 27 are connected to lances 15. The container receiving means 7 is grounded for the plasma treatment, the alternating voltage of AC voltage generators 27 being likewise referred to earth potential. Thus, lances 15 define a first electrode, and the inner wall of container receiving chambers 71 define the second electrode.

It is generally favorable, as in the example shown in FIG. 4, to provide a separately controllable high-frequency power source or AC power source for the electrodes of each of the container receiving chambers, preferably a high voltage source with a frequency in the medium frequency range from 0.1 to 200 kHz. This is advantageous, since in this manner the energy input for each plasma chamber may be controlled separately, for example through the plasma flow, so that in all plasma chambers the plasma intensity will be the same.

Alternatively, excitation of the low-pressure plasma may be accomplished by microwaves, preferably in a range around 2.45 GHz, or by radio frequency in a range around 13.56 MHz.

In order to produce a uniform glow discharge which moreover achieves a deep cross-linking of the organic film, generally, without limitation to the exemplary embodiments shown in the figures, the following parameters have been found to be favorable for generating the plasma:

The medium-frequency voltage applied to the electrodes preferably ranges from 0.5 kV to 10 kV, more preferably from 0.8 kV to 3 kV.

For the plasma discharge in a container, a current is preferably set in a range from 1 mA to about 200 mA.

The invention permits to ensure in a surprisingly simple manner that a homogeneous surface treatment is possible in particular for cylindrically symmetric containers by using a preferred embodiment of the apparatus:

The apparatus in this case comprises at least one centering means which enables to center the container receiving means and the transfer means. In other words, a centering means is provided by means of which the container receiving means can be centered relative to the treatment tools at the treatment stations in a plane perpendicular to the lifting direction of the treatment tools.

Furthermore, in a preferred embodiment the invention comprises a method in which the treatment tools are positioned in an axially symmetric relationship to the containers or guided in axially symmetric manner during the surface treatment. For example, the internal electrodes are introduced into the containers in axially symmetric manner and especially are also positioned in an axially symmetric relationship. In another example, the spray nozzles are positioned in axially symmetric relationship and during the surface treatment are guided in axially symmetric manner with respect to the containers, preferably at a constant speed.

Generally, it is furthermore advantageous both for producing a homogeneous field and for a homogeneous distribution of the process gas, to have the electrodes or lances 15 centered by appropriate means such as centering or positioning means, so that lances 15 extend along the central axis of the syringe barrels 250. The same applies to the spray nozzles. The latter are likewise preferably centered relative to the central axis of the syringe bodies or, more generally, of the containers to be coated, in order to obtain a uniform thickness of the organic film. The centering may be effected, for example, using at least one adjustable clamping means, which centers the electrodes or spray nozzles in axially symmetric relationship to the containers accommodated in the container receiving means. In a modification of the invention, at least one adjustable clamping means may be provided as a part of the centering means, which centers the transfer means along with the container receiving means with respect to the treatment tools in an axially symmetric relationship.

For example, the adjusting screws of the clamping means may be sealed following the positioning to ensure that the position is not changed during operation. According to another embodiment, however, it is likewise possible to use a self-centering component which is positioned appropriately.

Figure 5:
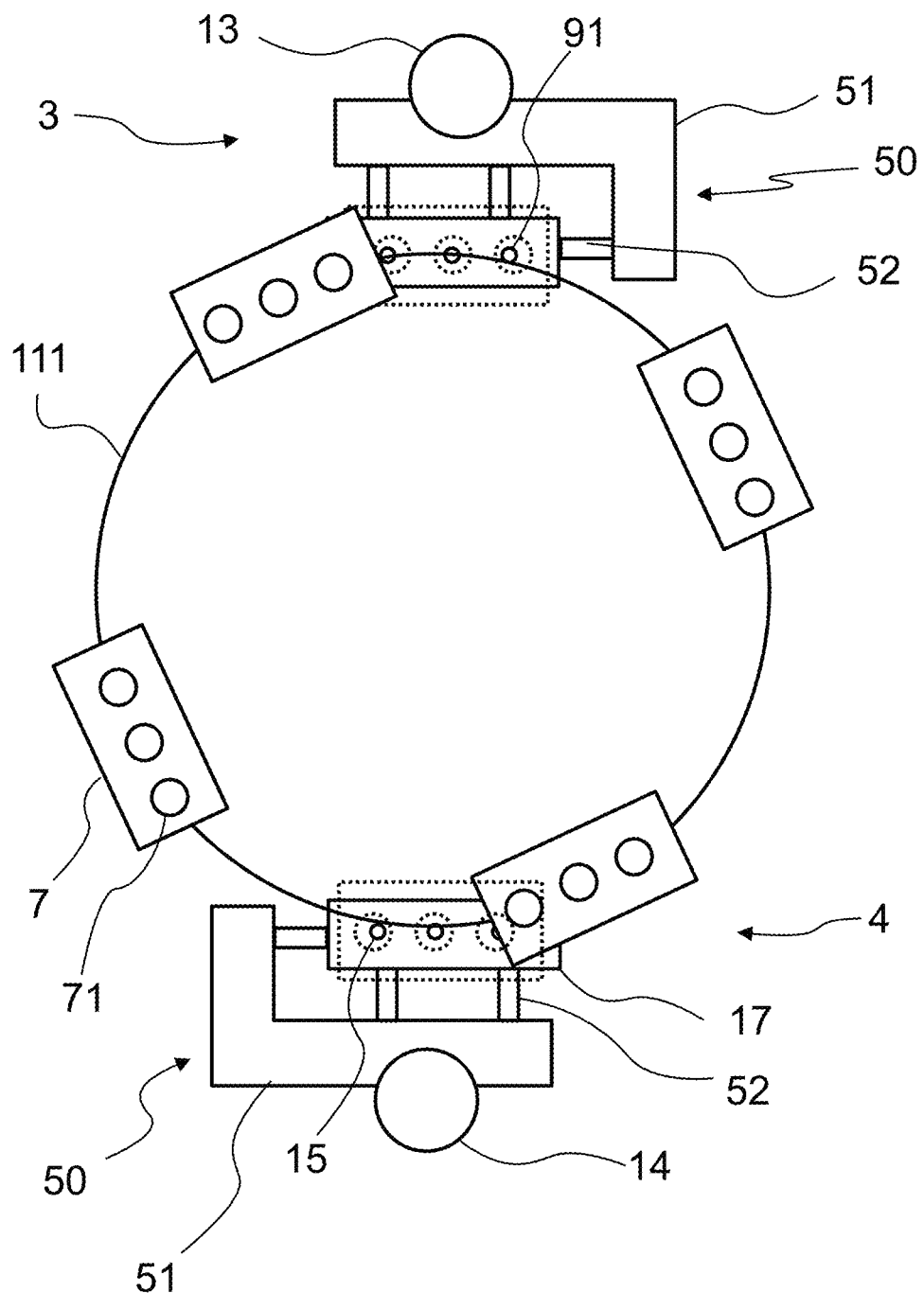
FIG. 5 shows an exemplary embodiment of an apparatus 1 for plasma treatment including centering means.

FIG. 5 illustrates one embodiment of an apparatus 1 for plasma treatment according to the invention. Here, apparatus 1 is shown in a plan view. The transfer means 11 is configured as a carousel or circular rotary table 111. Container receiving means 7 are arranged on circular rotary table 111 and are conveyed therewith along a circular path to treatment stations 3, 4. In this exemplary embodiment, each of treatment stations 3, 4 has a centering means 50. Each of centering means 50 comprises a bracket 51 attached to the respective lifting device 13 or 14, respectively. The treatment tools, here specifically spray nozzles 91 and the plasma treatment tool including closing element 17 and lances 15 are connected to the bracket by means of adjusting screws 52. Adjusting screws 52 are arranged so that the treatment tools are displaceable in a plane perpendicular to the lifting direction of lifting devices 13, 14. Adjusting screws 52 are adjusted such that the respective treatment tools, specifically lances 15 and spray nozzles 91, are positioned at the intended holding positions of the container receiving means 7 (which are shown in dotted lines) in an axially symmetric relationship to the longitudinal axes of the containers accommodated in container receiving chambers 71. Adjusting screws 52 are fixed using suitable clamping means. Alternatively or in addition, the rotational axis 112 of circular rotary table 111 may be adjusted in a direction perpendicular to the lifting direction using appropriate centering means.

Figure 6:
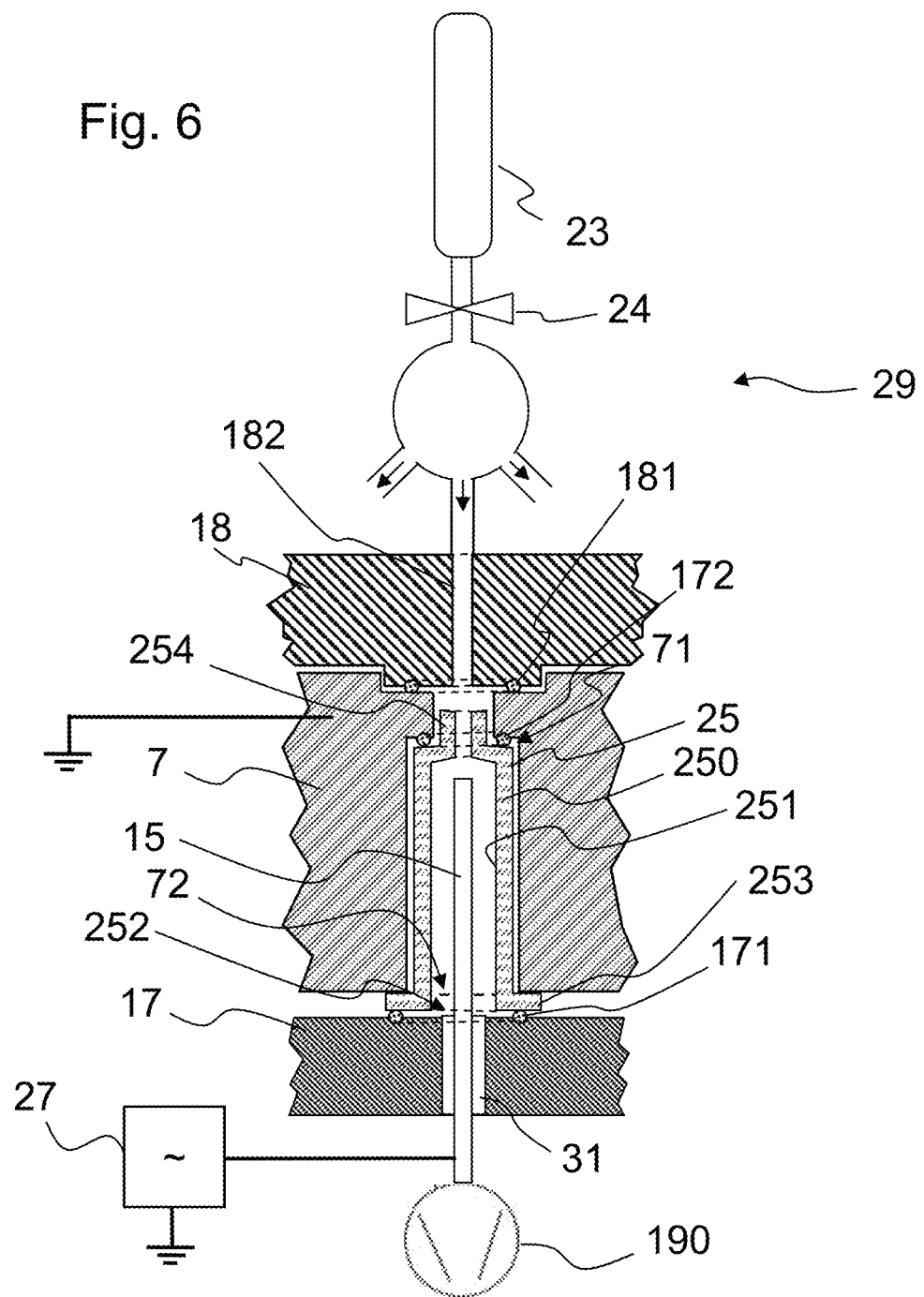
FIG. 6 illustrates parts of the embodiment shown in FIG. 4, with the plasma reactor closed.

FIG. 6 shows a detail of apparatus 1, with the container receiving means 7 in treatment station 4, and with the closing elements 17, 18 brought together with container receiving means 7 to form a plasma reactor.

To form a gas-tight joint, a sealing element 181 is provided between upper closing element 18 of gas manifold 29 and container receiving means 7, which seals the gas inlet passage 182 of closing element 18 that is in communication with syringe nozzle 254 from the ambient atmospheric pressure.

Lance 15, which has an alternating voltage generator 27 connected thereto, is electrically insulated from closing element 17 by an insulating element. The container receiving means or at least the inner wall of container receiving chamber 71 are coupled to ground potential, which is also the reference potential of AC voltage generator 27, so that due to the alternating voltage applied an alternating electric field or electromagnetic field is formed between the inner wall of container receiving chamber 71 and lance 15.

According to a preferred embodiment of the invention, a pulsed plasma is generated. This may be achieved by employing a pulsed AC voltage. The pulse frequency thereof is preferably at least 10 times smaller than the frequency of the alternating voltage. In a particularly preferred embodiment, the pulsed plasma may also be generated by applying a continuous AC voltage. It was found that by positioning a dielectric body, especially simply in form of the substrate itself, between the two electrodes, a pulsed plasma zone may be produced within the container in a surprisingly simple way.

Generally, the following process parameters are particularly favorable for good adhesion and surface properties:

The surface treatment of the organic layer is performed using a pulsed plasma with a duty ratio of $T=P_{on}/(P_{off}+P_{on})<0.5$. In other words, the duration of a pulse is less than half of the duration of a pulse cycle period comprising the pulse and the pulse interval. What follows therefrom is that the pulse durations are shorter than the pulse intervals. A particularly preferred duty ratio is $T=P_{on}/(P_{off}+P_{on})<0.3$. This duty ratio is advantageous for a controlled small energy input for efficiently cross-linking the layer, for preventing excessive hardening or even overheating of the lubricating layer and the container, and for a longer gas flow period to remove volatile compounds between the pulses in order to minimize contamination of the layer.

FIG. 7 shows a detail of a container receiving means 7 according to still another modification of the invention which may be combined with all embodiments of the invention. The specific embodiment shown in FIG. 7 is based on the arrangement shown in FIG. 3. In this embodiment of the invention, the container receiving chambers 71 are not directly defined in the body of container receiving means 7. Rather, container receiving chambers 71 are at least partially defined by the inner surfaces of container receiving sleeves 37 which in turn are inserted into fitting receptacles 38 in the container receiving means 7. This offers the advantage that container receiving means 7 may be used for different sizes of containers to be treated, such as syringes of different filling volumes. As is furthermore shown in FIG. 7, the inner surface of container receiving sleeve 37 may be adapted to the different outer diameters of the containers, in the present case the outer diameters of syringe barrel 250 and nozzle 254, to avoid large clearances to the outer surface of the container. Additionally, container receiving sleeve 37 serves to center the container to be treated in its intended position, so that the treatment tools, in particular the spray nozzle and/or an internal electrode and/or a gas lance are introduced in concentric relationship to the container's longitudinal axis.

According to a yet another modification of the invention, the inner surface of container receiving chamber 71 is at least partially formed by a dielectric material. Preferably the dielectric constant thereof ranges from 1.2 to 80. In the simplest case, a container receiving sleeve of dielectric material 37 or having an inner lining of dielectric material is used for this purpose. More preferably, a plastic material is used as the dielectric material. Surprisingly, ignition of a plasma is readily possible even with this additional dielectric material between the electrodes, in addition to the typically dielectric container.

FIG. 8, by way of example, shows parts of the apparatus 1 according to yet another embodiment of the invention. Specifically, a container receiving means 7 loaded with syringe bodies 25 is shown in plasma treatment station 4, with the closing element brought together with container receiving means 7 to form a plasma reactor in such a manner that the syringe bodies 25 are sealed at the plunger openings thereof by sealing elements 171.

This exemplary embodiment of the invention illustrated in FIG. 8 is based on an arrangement in which the electromagnetic field in the plasma zone inside the containers is generated by at least two electrodes which are disposed outside the container. Specifically, as is the case in the embodiment shown in FIG. 8, electrodes 40, 41 may be arranged axially along the container axis, i.e. axially offset at different distances from the container opening. This embodiment of the invention offers the advantage that the field is produced without an internal electrode. This allows to produce a field in areas which are otherwise difficult to access by means of an internal electrode. When plasma treating syringe bodies 25, this even permits to treat the inside of the Luer taper or nozzle 254 of the syringe body 25 in this manner.

Advantageously in this case, as in the example shown in FIG. 8, electrodes 40, 41 together may produce the field in a plurality of container receiving chambers 71. To this end, the two electrodes 40, 41 are connected to a common power supply in form of an AC voltage generator 27, via an electric coupling means 270. Preferably at least one of the electrodes, more preferably, as illustrated in FIG. 8, both of electrodes 40, 41 are part of the container receiving means 7.

Electrodes 40, 41 are arranged to be separated from each other in axial direction by an insulator 42 and have openings 43 which enclose the container receiving chambers 71.

According to a further modification of the invention, without being limited to the embodiments described below with reference to the further figures, additional treatment stations may be provided. For example, in yet another embodiment of the invention a two-layered inner coating of the containers may be provided. In this case, the layer applied first may improve adhesion of an overlying lubricating layer, i.e. the layer subsequently applied. For this purpose, the apparatus according to the invention may comprise a first treatment station including means for applying a first organic film, preferably by spray-depositing, a second treatment station downstream of the first treatment station in the transfer direction, which includes means for generating a low-pressure plasma in the interior of the containers, a third treatment station for applying a further organic film, the third treatment station being arranged downstream of the second treatment station in the transfer direction, and a fourth treatment station downstream of the third treatment station in the transfer direction, including a further means for generating a low-pressure plasma in the interior of the containers.

According to yet another embodiment of the invention, generally, a treatment station for drying the deposited organic film prior to the plasma treatment may be provided as a further treatment station. Like the deposition of the organic film and the plasma treatment, the drying may be accomplished using tools or components that are brought together with the container receiving means 7 using a lifting device. For example, a lance may be introduced into the containers for drying the organic film, by means of which the container interior is purged with a gas, preferably compressed air. This purging removes the substances outgassing during drying, such as solvents. Alternatively or additionally, a heating means may be introduced in order to accelerate the drying of the organic film.

A two-layered coating of which at least one of the layers, preferably both organic layers has/have been cross-linked by being subjected to the respective low-pressure plasma, and which can be produced with the apparatus described above, is particularly suitable as a lubricating film on pharmaceutical packagings made of glass. For this purpose, according to one embodiment of the invention, the apparatus comprises a further treatment station for pre-treatment, which is configured as a spray-depositing station, in which an intermediate layer is applied to the inner surface of the container. What follows when the intermediate layer has been applied is a drying and/or curing step during which volatile components from the intermediate layer are removed from inside the container, at least largely, preferably by a subsequent treatment step in form of a heat treatment, a spraying process using compressed air, or in form of an evacuation process.

One example is shown in FIG. 9. Herein, apparatus 1 includes a total of five treatment stations. The last two treatment stations 3, 4 correspond to the treatment stations 3, 4 described above for applying an organic film, especially a silicone-free film (treatment station 3) and for cross-linking the film in the low-pressure plasma (treatment station 4).

However, before applying the organic lubricating layer, an intermediate layer is applied in treatment stations 3A, 5, and 4A. This layer serves to ensure good adhesion of the lubricating layer on the inner surface of the container. In treatment station 3A, a film is spray-deposited using spray nozzles 91, and in treatment station 4A it is treated by a low-pressure plasma. Interposed between treatment stations 3A, 4A is a further treatment station 5. This treatment station likewise comprises treatment tools 9 which are brought together with container receiving means 7 by a lifting device 13. Here, compressed air lances 92 are used as the treatment tools 9, by means of which the interior of the containers is purged in order to dry the organic film. According to an alternative or additional embodiment, it is also possible to introduce heating mandrels 93 into the containers, as the treatment tools 9, in order to dry or cure the layers.

By way of example, plasma treatment stations 4A, 4 are configured similar to the embodiments illustrated in FIGS. 4 and 6 in which the process gas is supplied through a further closing element 18 opposite closing element 17. It is also possible for treatment stations 4, 4A to be configured similar to the embodiments illustrated in FIGS. 1, 2 and 3.

FIG. 10 illustrates a variation of the embodiment shown in FIG. 9. Instead of drying the organic material of the intermediate layer using compressed air lances 92 which are introduced into the syringe body by a lifting device 13, drying is accomplished in an inline furnace 45. In this case, container receiving means 7 loaded with the containers, or here specifically with the syringe bodies, is passed through inline furnace 45 by the transfer means.

Some exemplary embodiment of the method performable using an apparatus 1 as described above will be set out below.

Exemplary Embodiment 1

Four washed and dried glass syringe bodies 25 made of borosilicate glass (of the Fiolax clear type), size 1.25 ml, are placed in a container receiving means 7 according to the embodiment shown in FIGS. 4 and 5 having four container receiving chambers 71, and are fixed by retaining means. The Luer taper of each syringe is sealed from atmospheric pressure in the region of the upper openings by a respective sealing element 172. Container receiving means 7 is placed in apparatus 1 and is transferred horizontally to treatment station 3, by the transfer means. Here, syringe bodies 25 are oriented with the Luer taper or nozzle 254 vertically upwards (i.e. in the 12 o'clock direction).

Container receiving means 7 is brought to a stop position and is positioned so that the central axes of the syringe bodies 25 are oriented centrally to the extended axes of spray nozzles 91 which are configured as two-substance nozzles. By means of pneumatic lifting device 13, the four two-substance nozzles are simultaneously brought together with the container receiving means 7 in a vertical direction and are thereby introduced into the interior of the syringe bodies.

In a dynamic process during which the spray nozzles 91 are driven into the syringe bodies 25, the inner surface of the syringe barrel 250 is coated with a silicone-free organic layer using a two-phase flow including nitrogen and a perfluoropolyether fluid of the Fomblin M100 type. Each spray process is carried out with a duration of 1.4 s, with a gas mass flow of 84.5 mg/s, whereby a surface-related amount of substance of 0.07 microliters per square centimeter is applied to the inner surface of each syringe body 25. During the spraying operation, the spray nozzles are retracted from the syringe bodies 25 at a constant speed.

Immediately after the spraying process has been completed and the spray nozzles have been retracted to their starting positions, container receiving means 7 including the syringes pre-coated with the fluid film is transferred to treatment station 4 and brought to the intended stop position within a period of less than 5 seconds, by transfer means 11 configured as a circular rotary table.

In treatment station 4, closing element 17 which has four hollow electrodes including sealing rings attached thereto is directed towards container receiving means 7 in the vertical direction, by lifting device 14. On the opposite end, the further closing element 18 which has a symmetric gas manifold 29 with four gas lines connected thereto, is directed towards container receiving means 7 by lifting device 12. Sealing is accomplished using four further sealing elements 181 in form of sealing rings which are arranged on container receiving means 7.

After closing elements 17, 18 have been applied, a plasma reactor chamber is formed together with container receiving means 7 and the syringe bodies 25, which is gas-tight relative to atmospheric pressure. Furthermore, an electrical connection is established between the electrodes of container receiving means 7 and the AC voltage generators in form of high voltage medium frequency generators.

Subsequently, the reactor chamber is evacuated to a basic pressure below 0.5 mbar using a vacuum pump 190, and then pure argon gas is introduced into the plasma reactor via gas manifold 29. The entire molecular flow for all reactor chambers is controlled using a mass flow controller, and is symmetrically distributed to all of the four reactor chambers. By means of a throttle valve, a process pressure is adjusted to 5 mbar.

Then, electric power in a range from 140 W to 560 W (1 W=1 VA) is supplied by the medium frequency generators at a frequency of 100 kHz, separately at each of the individual electrodes of the plasma chambers, so that a low-pressure glow discharge is ignited and maintained in the plasma chambers. The simultaneous plasma treatment of the fluid films on the surfaces of syringe bodies 25 is performed for a period of 5 seconds. Within this period, the silicone-free lubricating films on the syringe surfaces are cured simultaneously.

Subsequently, the reactor chamber is purged with nitrogen gas. Container receiving means 7 is locked out from treatment station 4, and syringe bodies 25 are removed from the container receiving means 7.

The following tests have been carried out on the glass syringes coated with the silicone-free lubricating layer:

Immediately following the production of the silicone-free lubricating layers, silicone-free stoppers of the Helvoet FM257 type are inserted into a first part of the syringes, and static and dynamic frictions are determined.

Figure 11:
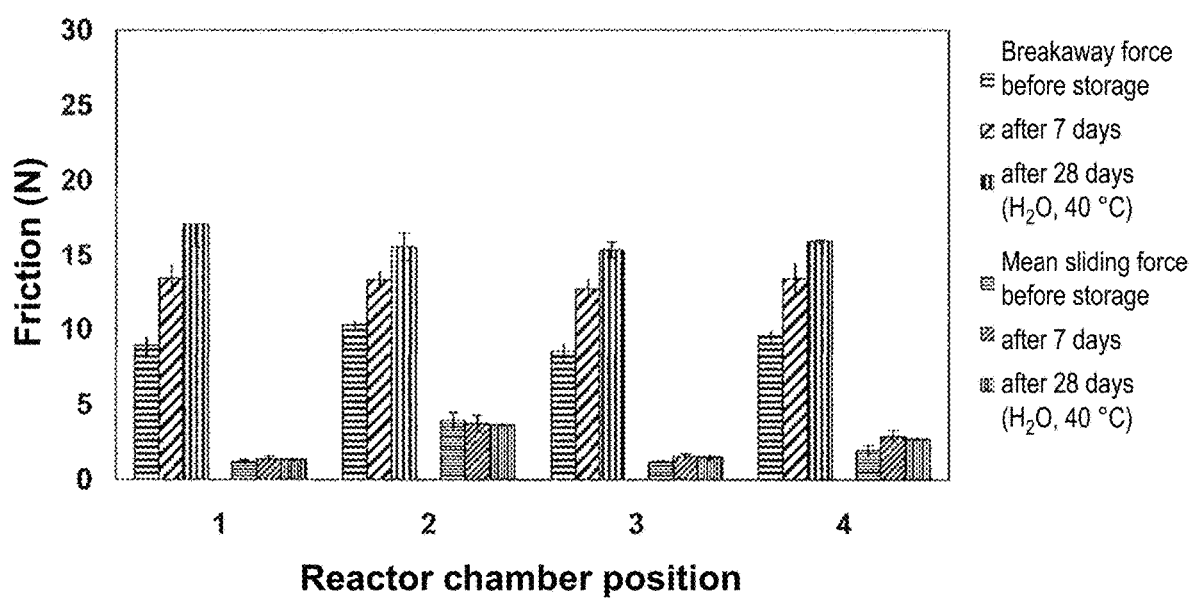
FIG. 11 shows measurement results of breakaway force and mean sliding force for moving a plunger within a syringe body coated with a lubricating layer.

Another part of the silicone-free glass syringes is filled with water, provided with a sealing cap for the nozzle, also known as "tip cap", and is then closed with the same stopper and stored at a temperature of 40° C. for periods of 7 days and 28 days. Afterwards, static and dynamic frictions after storage are also measured on these water-filled syringes. The syringes are numbered in a manner so that they can be associated to the individual positions of the spray-deposition and plasma treatment system. The measured data of static and dynamic frictions are plotted in FIG. 11.

The breakaway forces before storage are in a range from 9 N to 10 N for all lubricating layers produced at positions 1-4, and exhibit an increase after storage typical for lubricating layers. After 28 days of storage at 40° C., the breakaway force is in a range from 15 N to 17 N. The dynamic friction data of the syringes are in a range from 1 N to 4 N for all reactor chambers, and in particular are stable during the storage period.

The test results show that the inventive apparatus 1 enables to produce silicone-free lubricating layers in a process suitable for mass production due to the simultaneous treatment of a plurality of syringe bodies, and that thereby, even with non-siliconized stoppers, breakaway and sliding forces are achieved which meet the requirements for an application of the pharmaceutical primary packaging. In particular, the lubricating layers produced in the multi-position apparatus according to the method of the invention exhibit storage stability in the area of the contact surface to water, which becomes evident from the constant and very low dynamic friction.

Exemplary Embodiment 2

Four syringe bodies 25 made of COC (cyclo-olefin copolymer), size 2.25 ml, are placed in a container receiving means 7 according to the embodiment shown in FIGS. 4 and 5 having four container receiving chambers 71, and are fixed by retaining means. The Luer taper of each syringe is sealed from atmospheric pressure in the region of the upper openings by a respective sealing element 172. Container receiving means 7 is placed in apparatus 1 and is horizontally transferred to treatment station 3 and brought to a stop position.

Similar to the first example, a silicone-free perfluoropolyether fluid is spray-deposited to the inner surface of the COC syringe barrels 25. Immediately after the spraying process has been completed and spray nozzles 91 have been retracted to their starting positions, container receiving means 7 including the pre-coated syringes is transferred to treatment station 4 and is brought to the intended stop position within a period of less than 5 seconds, by the circular rotary table.

In treatment station 4, closing element 17 which has four hollow electrodes including sealing rings attached thereto is directed towards container receiving means 7 in vertical direction, by lifting device 14. On the opposite end of container receiving means 7, closing element 18 which has the gas manifold 29 with four gas lines connected thereto, is directed towards container receiving means 7 by lifting device 12, and is joined thereto using four further sealing rings 172 provided on container receiving means 7.

After closing elements 17, 18 have been joined with container receiving means 7, plasma reactor chambers are formed, which are gas-tight relative to atmospheric pressure. Furthermore, an electrical connection is established between the electrodes of container receiving means 7 and the high voltage generators.

Subsequently, the reactor chamber is evacuated to a basic pressure below 0.5 mbar using a vacuum pump, and then pure argon gas is introduced via gas manifold 29. Similar parameters as in exemplary embodiment 1 are applied for the plasma process, so that the fluid films on the COC syringe bodies 25 are simultaneously cross-linked by the plasma.

Then, the reactor chamber is purged with nitrogen gas. Container receiving means 7 is locked out from treatment station 4, and the syringe bodies are removed.

Similar tests as in exemplary embodiment 1 for static and dynamic friction have been carried out on the COC syringes coated with the silicone-free lubricating layer. It has been found that the same good static and dynamic friction properties of the silicone-free lubricating layers as on glass syringes can be achieved on COC syringe bodies.

Exemplary Embodiment 3

Four glass syringes according to the above exemplary embodiment 1, size 1.25 ml, are placed in a container receiving means 7 having four container receiving chambers 71, and are fixed by retaining means. The glass syringes are coated with two layers in a multi-step manufacturing process according to the apparatus shown in FIG. 9. Similar to exemplary embodiment 1, very low friction coefficients are achieved for the two-layer coated glass syringe bodies. As a process for drying and adhering the first layer, both a method using compressed air lances 92 as well as using heating mandrels 93 has proved to be efficient.

Exemplary Embodiment 4

Four glass syringes according to the above exemplary embodiment 1, size 1.25 ml, are placed in a container receiving means 7 having four container receiving chambers 71, and are fixed by retaining means. The glass syringes are provided with a two-layer coating in an apparatus 1 according to the apparatus 1 shown in FIG. 10 which includes a inline furnace 45 for drying and adhering the intermediate layer. Similar to exemplary embodiment 1, very low friction coefficients are achieved.

Exemplary Embodiment 5

Glass syringes are inserted into a container receiving means 7 according to FIG. 7, into a respective opening of the two outer electrodes, and are spray-coated similar to exemplary embodiment 1 with a silicone-free Fomblin M100 fluid, in treatment station 3. Subsequently, container receiving means 7 is transferred to treatment station 4 according to FIG. 7, and the syringe bodies 25 are gas-tightly sealed from outer atmospheric pressure by means of closing elements 17, 18, and are connected to vacuum pump 190 and gas manifold 29. After pre-evacuation of the syringe bodies 25 process gas is introduced into the syringe bodies 25 similar to exemplary embodiment 1. By applying a radio frequency AC voltage (RF voltage) at a frequency of 13.56 MHz to the two outer electrodes, a plasma is simultaneously ignited in syringe bodies 25 thereby curing the silicone-free lubricating coating.

LIST OF REFERENCE NUMERALS

1 Apparatus for plasma treatment
3, 4, 3A, 4A, 5, Treatment stations
7 Container receiving means
9 Treatment Tool
11 Transfer means
12, 13, 14 Lifting device
15 Lance
17, 18 Closing element
19 Means for evacuating syringe barrels
20 Vacuum connection
23 Process gas reservoir
24 Metering valve
25 Syringe body
27 AC voltage generator
29 Gas manifold
31 Insulation element
33 Light guide
35 Photodetector
37 Container receiving sleeve
38 Receptacle for 37
40, 41 Electrodes
42 Insulator between 40 and 41
43 Opening in 40, 41
45 Inline furnace
50 Centering means
51 Bracket of 50
52 Adjusting screw
71 Container receiving chamber
72 Open end of 71
91 Spray nozzle
92 Compressed air lance
93 Heating mandrel
111 Circular rotary table
171, 172,
181 Sealing element
175 Gas conduit
182 Gas inlet passage
190 Vacuum pump
191 Valve
192 Suction opening in 7
250 Syringe barrel
251 Inner surface of syringe barrel
252 Plunger opening
253 Flange
254 Nozzle of 25
270 Electric coupling means

The invention claimed is:

1. A pharmaceutical container, comprising:
a wall having an inner surface;
an intermediate layer on the inner surface;
a lubricating layer that a cross-linked organic film and is silicone free on the intermediate layer, the intermediate layer adhering the lubricating layer on the inner surface; and
a stopper in contact with the lubricating layer,
wherein the stopper has an initial breakaway force with respect to the lubricating layer that is in a range from 9 N to 10 N,
wherein the stopper has a sliding force with respect to the lubricating layer from 1 N to 4 N and the sliding force is stable within 7 days of storage at 40° while the pharmaceutical container is filled with water.

2. The pharmaceutical container of claim 1, wherein the sliding force is stable within 28 days of storage at 40° while the pharmaceutical container is filled with water.

3. The pharmaceutical container of claim 1, wherein the sliding force does not vary more than 50% before and after storage.

4. The pharmaceutical container of claim 1, wherein the wall comprises a material selected from a group consisting of glass, cycloolefin copolymers (COC), cyclo-olefin polymers (COP), HDPE, MDPE, LDPE, polypropylene, and borosilicate glass.

5. The pharmaceutical container of claim 1, wherein the stopper has a breakaway force with respect to the lubricating layer that is, after storage for 7 days at 40° C. while the pharmaceutical container is filled with water, greater than 0 N and at most 15 N.

6. The pharmaceutical container of claim 1, wherein the stopper has a breakaway force with respect to the lubricating layer that is, after storage for 28 days at 40° while the pharmaceutical container is filled with water, greater than 0N and at most 17N.

7. The pharmaceutical container of claim 1, wherein the intermediate layer is a crosslinked organic film.

8. The pharmaceutical container of claim 7, wherein the crosslinked organic film comprises a material selected from a group consisting of perfluoropolyether (PFPE), perfluorosiloxane, PTFE particles, mineral oil, vegetable oil, animal based oil, synthetic fluid hydrocarbons, fluid fluorinated or chlorinated hydrocarbons, organic esters, fatty acid esters, polyphenylethers, phosphoric acid esters, polyethylene glycol, polyalkylene glycols, polyalphaolefin, polyaromatic hydrocarbon, alkylbenzenes, polyurethanes, squalene, and combinations thereof.

9. A pharmaceutical container, comprising:
a wall with an inner surface coated with an intermediate layer and a lubricating layer that is silicone free on the intermediate layer, the intermediate layer adhering the lubricating layer to the inner surface; and
a stopper in contact with the lubricating layer;
an initial breakaway force of the stopper with respect to the lubricating layer that is in a range from 9 N to 10 N; and
a sliding force of the stopper with respect to the lubricating layer, wherein the sliding force is less than 5N.

10. The pharmaceutical container of claim 9, wherein the sliding force is stable within 7 days of storage at 40° C. while the pharmaceutical container is filled with water.

11. The pharmaceutical container of claim 9, wherein the sliding force is stable within 28 days of storage at 40° C. while the pharmaceutical container is filled with water.

12. The pharmaceutical container of claim 9, wherein the stopper has a breakaway force with respect to the lubricating layer, wherein the breakaway force does not increase more than 100% within 7 days of storage at 40° C. while the pharmaceutical container is filled with water.

13. The pharmaceutical container of claim 9, wherein the stopper has a breakaway force with respect to the lubricating layer, wherein the breakaway force does not increase more than 100% within 28 days of storage at 40° C. while the pharmaceutical container is filled with water.

14. Pharmaceutical packaging, comprising a plurality of a pharmaceutical containers, each of the plurality of a pharmaceutical containers comprising:
a wall with an inner surface coated with an intermediate layer and a lubricating layer that is silicone free on the intermediate layer, the intermediate layer adhering the lubricating layer to the inner surface; and
a stopper in contact with the lubricating layer; and
a sliding force of the stopper with respect to the lubricating layer,
wherein the sliding force of each of the plurality of pharmaceutical containers is less than 5 N, and wherein the stopper has an initial breakaway force with respect to the lubricating layer that is in a range from 9 N to 10 N.

15. The pharmaceutical packaging of claim 14, wherein the sliding force of each of the plurality of pharmaceutical containers is stable within 7 days of storage at 40° C. while the pharmaceutical container is filled with water.

16. The pharmaceutical packaging of claim 14, wherein the sliding force of each of the plurality of pharmaceutical containers is stable within 28 days of storage at 40° C. while the pharmaceutical container is filled with water.

17. The pharmaceutical packaging of claim 14, wherein the plurality of pharmaceutical containers comprise four pharmaceutical containers.

* * * * *